US00PP24639P3

(12) United States Plant Patent
Thome

(10) Patent No.: US PP24,639 P3
(45) Date of Patent: Jul. 15, 2014

(54) APPLE TREE NAMED 'B. THOME GALA'

(50) Latin Name: *Malus domestica*
Varietal Denomination: B. Thome Gala

(76) Inventor: Bernard J Thome, Comstock Park, MI (US)

( * ) Notice: Subject to any disclaimer, the term of this patent is extended or adjusted under 35 U.S.C. 154(b) by 143 days.

(21) Appl. No.: 13/507,917

(22) Filed: Aug. 7, 2012

(65) Prior Publication Data

US 2014/0047591 P1 Feb. 13, 2014

(51) Int. Cl.
*A01H 5/00* (2006.01)

(52) U.S. Cl.
USPC ..... Plt./162

(58) Field of Classification Search
USPC ..... Plt./162, 161
See application file for complete search history.

*Primary Examiner* — Anne Grunberg

(57) ABSTRACT

A new and distinct variety of Gala apple tree, Apple Tree named 'B. Thome Gala', originating as a whole tree mutation of the *Malus domestica* variety of 'Simmons', (U.S. Plant Pat. No. 10,840). This new variety is unique from its parent and other Gala cultivars in the prominent wide striping of the fruit and the heavy pink coloration in the blossom bud and petals.

3 Drawing Sheets

Latin name of the genus and species of the plant claimed: *Malus domestica.*

Variety denomination: 'B. Thome Gala'.

DESCRIPTIONS OF RELATED APPLICATIONS

The new variety, 'B. Thome Gala' differs from its parent, 'Simmons' (U.S. Plant Pat. No. 10,840) and other Gala varieties in the following characteristics:

A. The new variety differs from its parent 'Simmons' (U.S. Plant Pat. No. 10,840) in the broad configuration of its stripe and in the intense pink coloration of the blossom buds and blossoms.

B. The new variety differs from 'Burkitt Gala' (U.S. Plant Pat. No. 17,013) in its maturity date. The new variety ripens with other Gala cultivars while 'Burkitt Gala' (U.S. Plant Pat. No. 17,013) ripens 10 days earlier.

C. The new variety differs from 'Smith Gala' (U.S. Plant Pat. No. 14,448) in the bloom timing. 'Smith Gala' (U.S. Plant Pat. No. 14,448) blooms later than its parent and other Gala cultivars including the new variety.

D. The new variety differs from 'Banning Gala' (U.S. Plant Pat. No. 13,753) and all other known Gala cultivars in the intense pink coloration of the blossom buds and blossoms.

E. The new variety differs from 'McLaughlin Gala' (U.S. Plant Pat. No. 19,007) in the red coloration of its fruits.

BACKGROUND OF THE INVENTION

A new and distinct variety of Gala apple tree origination as a whole tree mutation of the *Malus domestica* variety of 'Simmons' (U.S. Plant Pat. No. 10,840) hereinafter referred to as the 'B. Thome Gala'. This new sport is unique from its parent and other Gala cultivars in the prominent wide striping on the fruit and the heavy pink coloration in the blossom buds and petals.

SUMMARY OF THE INVENTION

This new and distinct variety of Gala apple tree was discovered in 2003 as a whole tree mutation of 'Simmons' (U.S. Plant Pat. No. 10,840), in an orchard planted in 1999 near Comstock Park, Mich. The new variety was noticed because the fruit had a more prominent stripe and the buds and blossoms exhibited more pink coloration than the parent, 'Simmons' (U.S. Plant Pat. No. 10,840).

Observations during the next two seasons confirmed that the fruit colored with a bold, thick stripe as opposed to the parent which colors with a fine stripe. The blossoms and blossom buds of the new variety exhibited a much higher degree of pink coloration than the parent.

In August of 2003, buds were taken from the original tree and trees for further testing were reproduced by chip budding into M9 RN29, (US Plant Pat. No. 10,714) rootstock in Brentwood, Calif. The new variety has remained true to the description herein contained. The new variety has not been grown on its own root.

DESCRIPTION OF THE DRAWINGS

The accompanying photographs show typical specimens of the new variety as depicted in color as nearly true as is reasonably possible in color illustrations of this character. These specimens were obtained in Comstock Park, Kent County, Mich., 49345.

DETAILED BOTANICAL DESCRIPTION

Figure 1:
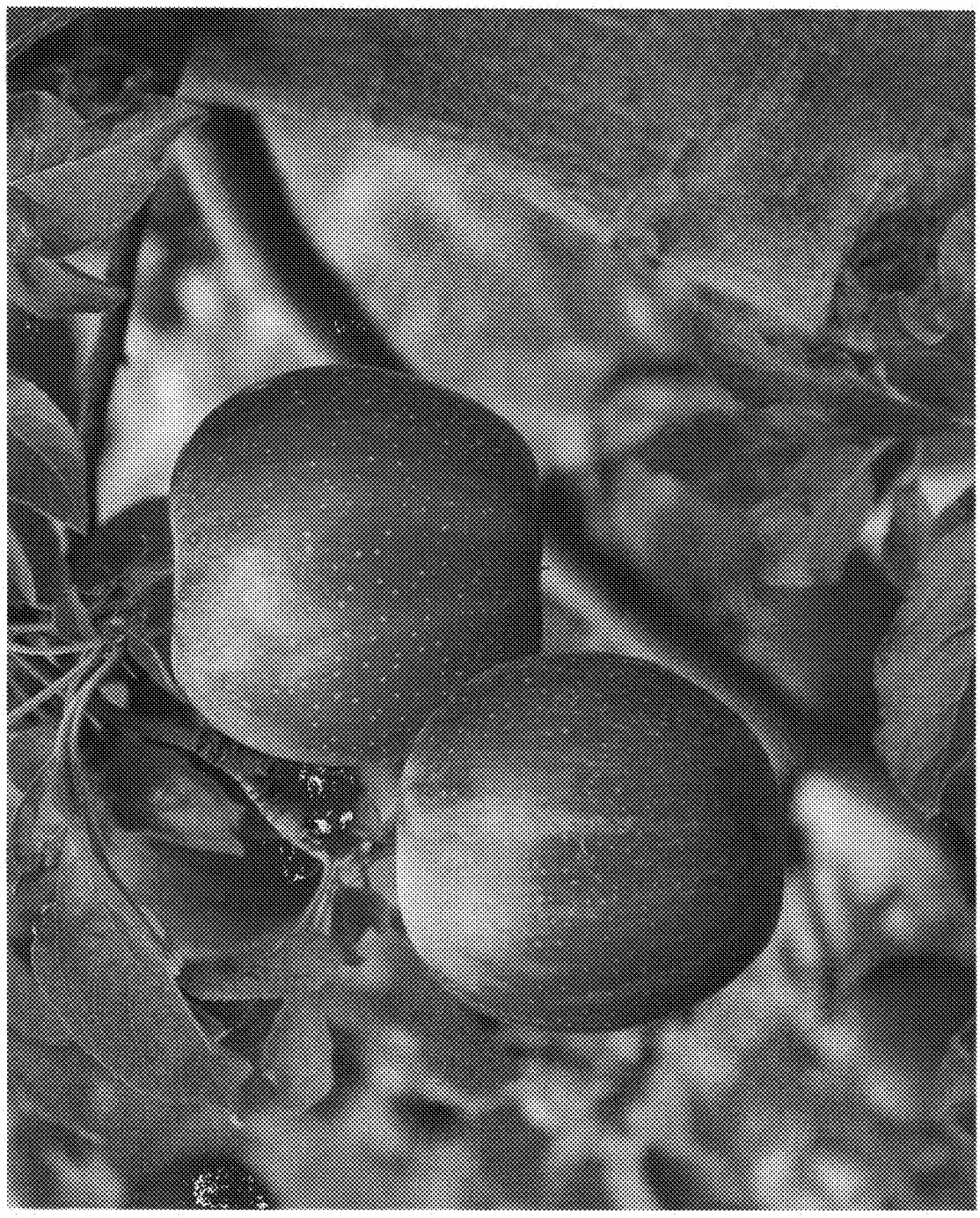
FIG. 1 illustrates the fruits and foliage of the new variety at maturity.
Figure 2:
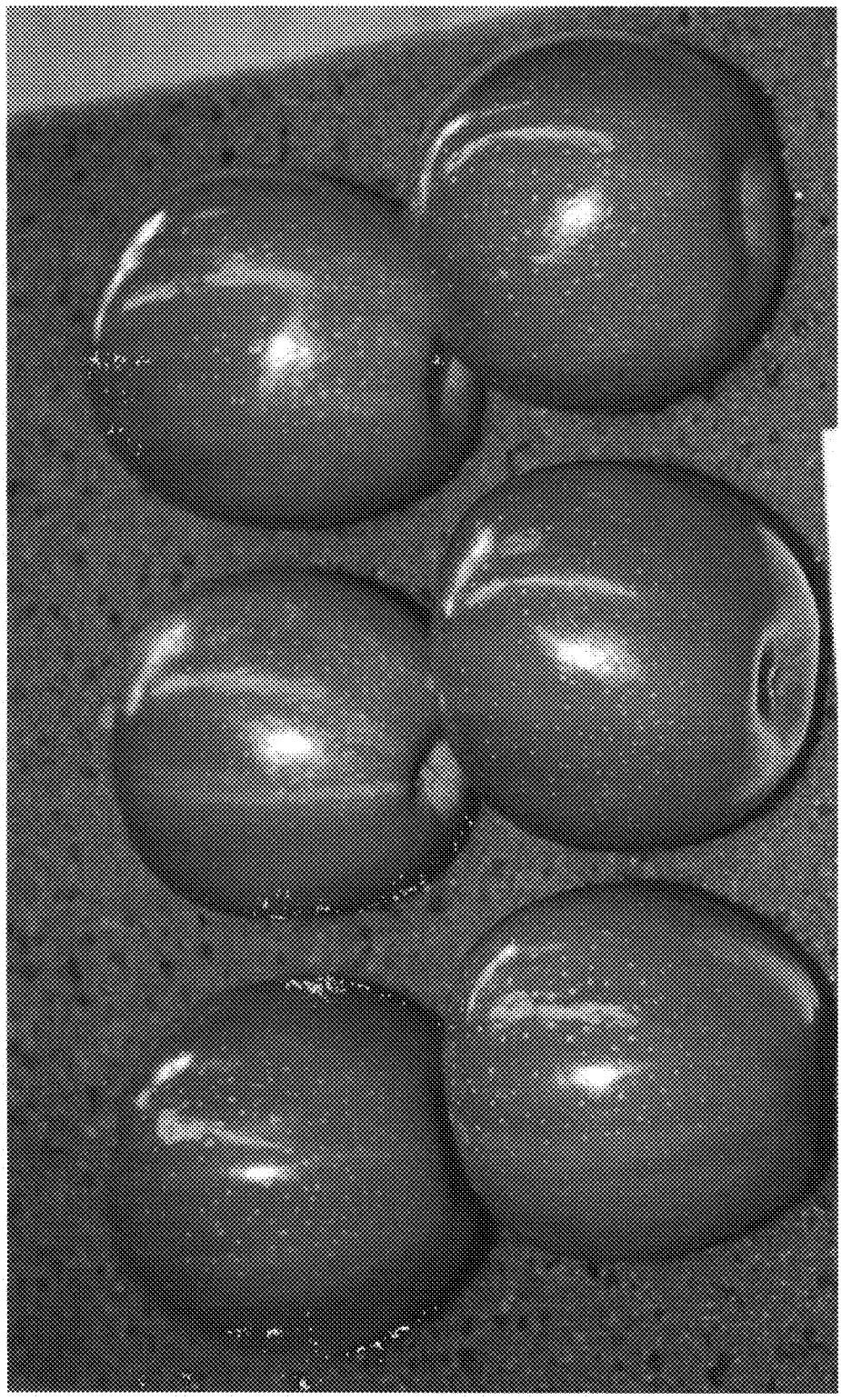
FIG. 2 illustrates 6 specimens of the fruit of the new variety showing the prominent stripe.
Figure 3:
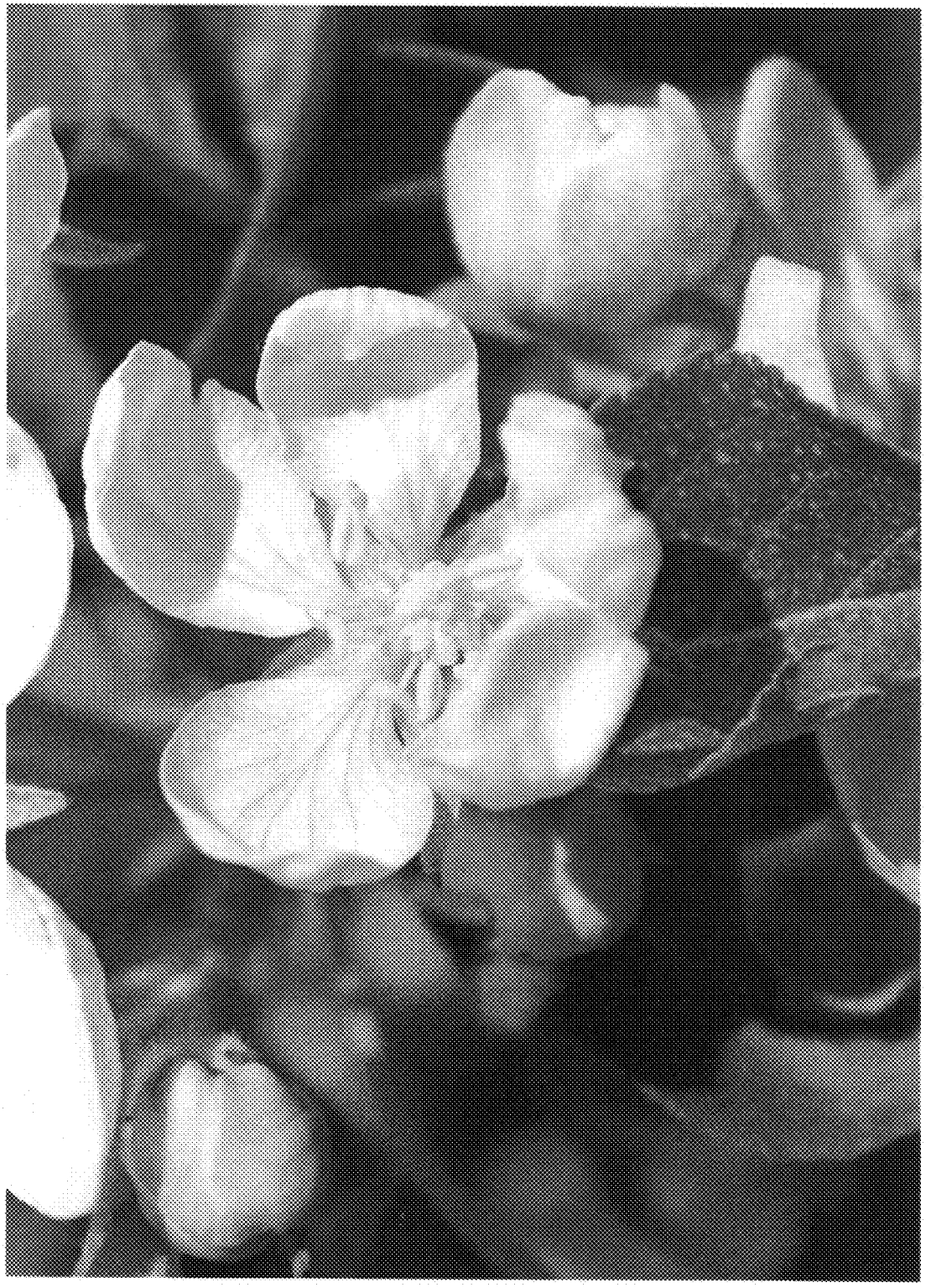
FIG. 3 illustrates blossoms of the new variety showing the pink coloration of buds and blossoms.

A detailed description of the 'B. Thome Gala' cultivar follows using The Royal Horticultural Society of London Colour Chart, 1986 edition, for color identification except where general color terms are sufficient.

Parentage: A whole tree mutation of 'Simmons' (U.S. Plant Pat. No. 10,840). Locality of the original discovery and observations is 1600 Eight Mile Road, Comstock Park, Mich. 49321.

Tree:
*Age.*—6 years.
*Size.*—Large, height 2.5 m, width 1 m.
*Vigor.*—Vigorous, yearly growth averages 1 m.
*Density.*—Medium.
*Form.*—Upright, spreading.
*Production.*—Very productive, averaging 800 bushels per acre.
*Growth type.*—Non-spur.
*Bearing.*—Annual.

Trunk:
*Diameter.*—68 cm at 40 cm above ground level.
*Bark.*—Smooth, color Grey 201C with an undercolor of Grayed Orange 165C.
*Lenticels.*—2 mm to 8 mm in length, 1 mm in width, color Grayed Orange 165C.

Branches:
5 *year old branch.*—28 mm in diameter, color Gray 201C.
4 *year old branch.*—16 mm in diameter, color Gray 201C.
3 *year old branch.*—11 mm in diameter, length 30 cm to 40 cm, color Gray 201C.
2 *year old branch.*—6 mm in diameter, length 25 cm to 40 cm, color Gray 201B.
1 *year old branch.*—1.5 mm to 2.0 mm in diameter, length 25 to 40 cm, color Grayed Purple 183A, lenticels 0.1 mm in diameter, round, color Grayed Yellow 161A.

Leaves:
*Size.*—Length 110 mm to 120 mm, width 75 mm to 85 mm.
*Texture.*—Leathery, crisp.
*Form.*—Broadly lanceolate.
*Base.*—Bluntly pointed.
*Apex.*—Bluntly pointed.
*Adaxial surface pubescence.*—None.
*Abaxial pubescence.*—Very fine.
*Adaxial surface color.*—Yellow Green 147A.
*Abaxial surface color.*—Yellow Green 147C.
*Venation.*—Pinnate, 10-12 veins, mainly alternate.
*Mid-vein.*—Mainly Yellow Green 151C.
*Margin.*—Serrate.
*Leaf glands.*—Absent.
*Petiole length.*—30 mm to 45 mm.
*Petiole width.*—2 mm.
*Petiole color.*—Yellow Green 14 B with some Red Purple 60B at base and at abscission layer.
*Petiole groove.*—None observed.
*Stipules.*—Very fine, at the base of the petiole on almost all leaves.
*Stipule length.*—7 mm.
*Stipule width.*—0.5 mm.
*Stipule color.*—Yellow Green 147B.

Leaf buds:
*Length.*—5 mm.
*Width.*—4 mm.
*Color.*—Grayed Purple 183A.
*Placement on branch.*—Tightly applied to the branch.
*Internode distance.*—30 mm.

Spurs: Present on $2^{nd}$ year and older wood.
*Length.*—6 to 8 mm.
*Width.*—4 to 6 mm.
*Color.*—Grayed Orange 177A.

Flowers: Mid-season bloom, May 13 in Comstock Park, Mich.
*Pollination requirements.*—Any diploid variety in the same season except pollen from golden delicious or any other gala sport.
*Presentation.*—Very showy.
*Fragrance.*—Fragrant.

Flowers at popcorn stage:
*Pedicle.*—Length 18 mm to 22 mm, diameter 2 mm.
*Pedicel color.*—Grayed Green 195A.
*Bud.*—Length 9 mm, width 7 mm to 8 mm.
*Bud color.*—Full blush of Red Purple 73B with background of White 155D.

Flowers at full bloom:
*Corolla diameter.*—Large, 75 mm to 85 mm when fully open.
*Number of flowers per cluster.*—3 to 5.
*Petals.*—Arrangement: free. Color: White 155D with a distinct blush throughout of Red Purple 73B, especially prominent around veins. Petal Veins: White 155D on 30% of petals, remaining petals showing distinct vein coloration of Red Purple 73B extending from base of petal to apex. Shape: Broadly ovate, base rounded to abruptly cuneate at junction with receptacle, apex rounded with slight tip. Entire petal is cupped. Basin is 5 mm deep. Margin: straight with occasional ruffling at the apex. Size: length 30 mm to 35 mm, width 20 mm to 25 mm. Texture: firm.
*Pedicel.*—Length 25 mm to 27 mm, width 2 mm, color Yellow Green 145D.
*Sepals.*—5 in number, wedge shaped, sharply pointed, length 5 mm, width 5 mm, color Yellow Green 145D.
*Filaments.*—Length 10 mm to 12 mm, width 0.3 mm, color White 155D at junction with anther.
*Anthers.*—Length 2 mm, width 1 mm, color Yellow 4C.
*Pistil.*—Held slightly lower than anthers in a majority of blossoms.
*Ovary.*—Length 4 mm, width 1.5 mm, pubescent, color Yellow Green 145D.
*Stigma.*—Width 1 mm, pubescent, color Green White 157C.
*Style.*—Length 3 mm, width 1 mm, color Green White 157C.

Fruit: Maturity when described, firm ripe.
*Harvest time.*—September 5 through 10 in Kent County, Mich.
*Size.*—Uniform, axial diameter 8 cm, transverse diameter 7.5 cm.
*Form.*—Globose.
*Cavity.*—Symmetrical, abrupt at base, apex acuminate, depth 1.5 cm, breadth 2 cm, markings none.
*Basin.*—Symmetrical, rounded, wide, breadth 2.5 cm, depth 1.5 cm, markings none.
*Calyx.*—Closed.
*Segments.*—Broadly lanceolate, reflexed from base at apex, approximate.
*Outer surface.*—Pubescent, color Grayed Green 191B.
*Inner surface.*—Pubescent, color Grayed Green 191C.
*Eye.*—Closed.

Skin: Thin, smooth, waxed, glossy.
*General color effect.*—Bright, prominent, wide red stripe over 100% of fruit, background red, very attractive appearance.

*Stripe*.—Averages 10 mm to 15 mm in width covering the entire length of the fruit. Color Red 46A to Red 45A.

*Background color*.—Yellow 8 B.

*Dots*.—Round, 1 mm in diameter, scattered throughout surface, color Yellow 8B.

*Flesh*.—Juicy, satiny.

*Color*.—Yellow Orange 19D.

*Texture*.—Firm, tender, fine, crisp.

*Flavor*.—Sweet, aromatic.

*Quality*.—Best.

Core:

*Bundle area*.—Small, oblate.

*Bundles*.—Inconspicuous, in one whorl.

*Core lines*.—Clasping, indistinct.

*Calyx-tube*.—Funnel form, glabrous toward base.

*Stem of funnel*.—Long.

*Depth of tube to shoulder*.—9 mm.

*Entire depth*.—21 mm.

*Auxiliary cavity*.—Present.

*Seed cells*.—Axial, open.

*Cell walls*.—Medium thin.

*Length*.—16 mm.

*Breadth*.—6 mm.

*Longitudinal section*.—Orbicular, obtuse at apex.

*Surface*.—Smooth.

*Cross section*.—Broad.

Seeds:

*Number perfect*.—6 to 10.

*Number in one cell*.—2.

*Length*.—7 mm.

*Breadth*.—4 mm.

*Color*.—Brown 200B.

Stem: Length 2.5 cm, breadth 6 mm at head decreasing to 4 mm at base, clubbed at head.

*Color*.—Grayed Orange 166B.

Use: Processing, fresh market, dessert.

Shipping quality: Good, subject to stem puncture.

Keeping quality: Excellent, 90 to 120 days in common storage, 6 months in controlled atmosphere storage.

Tree winter hardiness: Average for an apple variety. Tree is hardy to −20° to −25° F.

Bud winter hardiness: −10° to −15° F., depending on the stage of development of the bud.

Drought tolerance: Average for an apple variety. Normal requirements average ½" of rain per week. Severe drought adversely affects fruit size and quality.

Disease resistance: Susceptible to fire blight (*Erwinia amylovora*) and other bacterial diseases. Moderately susceptible to apple scab (*Venturia inaequalis*), powdery mildew (*Podosphaera leucotricha*), and other fungal diseases.

I claim:

1. A new and distinct variety of apple tree, *Malus domestica*, substantially as herein shown and described.

* * * * *